(12) United States Patent
Rindone et al.

(10) Patent No.: US 6,359,147 B1
(45) Date of Patent: Mar. 19, 2002

(54) REACTIONS CATALYZED BY CHROMIUM (III) CARBOXYLATES

(75) Inventors: Renato R. Rindone, Fair Oaks; W. Kenneth Musker, Davis, both of CA (US)

(73) Assignee: Dimension Technology Chemical Systems, Inc., Fair Oaks, CA (US)

( * ) Notice: Subject to any disclaimer, the term of this patent is extended or adjusted under 35 U.S.C. 154(b) by 0 days.

(21) Appl. No.: 09/445,736

(22) PCT Filed: Jun. 18, 1998

(86) PCT No.: PCT/US98/12251

§ 371 Date: Apr. 3, 2000

§ 102(e) Date: Apr. 3, 2000

(87) PCT Pub. No.: WO98/56500

PCT Pub. Date: Dec. 17, 1998

Related U.S. Application Data

(60) Provisional application No. 60/050,078, filed on Jun. 13, 1997.

(51) Int. Cl.[7] ............... C07C 67/02; C07C 327/22; C07C 69/66; C07C 69/38; C07C 69/02; C07D 207/40

(52) U.S. Cl. ............... 548/549; 560/129; 560/147; 560/179; 560/190; 560/231; 560/250; 548/547; 558/255

(58) Field of Search ............... 560/129, 147, 560/179, 190, 231, 250; 558/255; 548/547

(56) References Cited

U.S. PATENT DOCUMENTS

| | | | |
|---|---|---|---|
| 3,635,869 A | 1/1972 | Steele et al. | 260/30.4 EP |
| 3,644,223 A | 2/1972 | Hashimoto et al. | 252/431 X |
| 3,819,746 A | 6/1974 | Katzakian et al. | 260/830 |
| 3,838,101 A | 9/1974 | Steele et al. | 260/47 BN |
| 3,873,602 A | 3/1975 | Katzakian et al. | 260/475 P |
| 3,948,698 A | 4/1976 | Elrick et al. | 149/19 |
| 3,956,241 A | 5/1976 | Steele et al. | 260/47 BC |
| 3,962,182 A | 6/1976 | Steele et al. | 260/47 BN |
| 3,968,135 A | 7/1976 | Steele et al. | 260/438.5 R |
| 3,977,996 A | 8/1976 | Katzakian et al. | 252/431 C |
| 3,978,026 A | 8/1976 | Katzakian et al. | 252/431 C X |
| 4,017,429 A | 4/1977 | Steele et al. | 260/2 BP |
| 4,954,196 A | 9/1990 | DeHoff | 159/169 |

OTHER PUBLICATIONS

*Chemical Abstracts* (1993) 118(8) #61046w.
*Chemical Abstracts* (1986) 104(16) #131948d.
*Chemical Abstracts* (1986) 103(2) #6841s.
*Chemical Abstracts* (1983) 98(17) #142917b.
*Chemical Abstracts* (1982) 96(1) #5865c.
*Chemical Abstracts* (1981) 94(19) #156267u.
*Chemical Abstracts* (1980) 93(4) #27065g.
*Chemical Abstracts* (1972) 77(12) #76093t.
*Chemical Abstracts* (1972) 76(22) #127806s.
*Chemical Abstracts* (1967) 66(10) #38315g.
Kambara and Hatano, *J. Polymer Science* (1958) 27(115): 584–586.

*Primary Examiner*—Floyd D. Higel
(74) *Attorney, Agent, or Firm*—Townsend and Townsend and Crew LLP

(57) ABSTRACT

Reactions of ring systems, such as aziridines, oxetanes and oxiranes with carboxylic acids, anhydrides, imides, lactones and carbonate esters are catalyzed by $C_3$–$C_{60}$, substituted or unsubstituted, straight or branched-chained, alkyl, aryl, or aralkyl carboxylate $Cr^{+3}$ salts, preferably chromium +3 octoate. The catalysts also accelerate the reaction of hydroxy compounds with anhydrides, and of thiiranes with anhydrides. The catalysts selectively enhance the conversion of ring systems to form monomers, prepolymers, copolymers, functional end-group monomers, functional end-group prepolymers, and functional end-group polymers rather than forming homopolymers. By varying the catalyst concentration, molar ratios, and reaction temperatures, the reaction time required to form the desired product can be controlled.

9 Claims, No Drawings

REACTIONS CATALYZED BY CHROMIUM (III) CARBOXYLATES

CROSS REFERENCE TO RELATED APPLICATION

This application is a national stage of PCT/US98/12251 filed Jun. 18, 1998 and claims benefit of U.S. Provisional application No. 60/050,078, filed Jun. 13, 1997 for "Use of Chromium (III) Carboxylates as a Catalyst", the benefit of the filing date of which is hereby claimed under 35 USC §119.

TECHNICAL FIELD

This invention relates to the use of known chromium +3 carboxylates as catalysts for reaction of small ring systems, such as aziridines, oxetanes, lactones, carbonate esters, and thiiranes, and for reaction of hydroxy compounds with anhydrides in monomeric or polymeric reactions.

BACKGROUND ART

The literature is replete with information showing how to react epoxides with carboxylic acids, anhydrides and imides at room or elevated temperatures. As shown in *Catalysis in Polymer Synthesis,* ACS Symposium Series 496, Edited by E. J. Vandenberg (1992), aluminum porphyrins, mixed with quaternary salts of the type $R_4PX$ and $R_4NX$, are used to catalyze the reaction of an epoxy with carbon dioxide or anhydrides, but high temperature and/or long reaction times are generally needed. Elastomer modified epoxy resins such as diglycidyl ether of bisphenol A (DGEBA) can be made to react with carboxy-terminated polybutadiene-acrylonitrile (CTBN) using triphenyl phosphine, but high reaction temperature or long reaction time is needed to achieve complete reaction. There are a large number of amines, such as polyamide resins like Versamid®, diethylenetriamine, methylenedianiline, that are used to cure various epoxy systems but frequently the cure time is very long and accelerators, such as resorcinol, are required. Catalysts, such as the aluminum alkyls (which tend to be very pyrophoric) have been used to promote homo or block polymerization of epoxides, thioepoxides, selenoepoxides and oxetanes. Aziridines have been homopolymerized using a variety of acid catalysts. U.S. Pat. No. 3,635,869 (1972) discloses use of chromium+3 carboxylate salts to accelerate the reaction of epoxides with carboxylic acids, anhydrides and imides at room temperature or elevated temperatures.

General references to various catalytic systems include *Epoxy Resin Chemistry II,* ACS Symposium Series 221, Edited by R. S. Bauer (1983). However, such references do not show the use of chromium+3 carboxylates to catalyze ring systems with carboxy-containing compounds, such as carboxylic acids, anhydrides, imides, lactones and carbonate esters.

THE INVENTION

Summary

It is among the objects and advantages of the invention to employ chromium, $Cr^{+3}$, catalysts, particularly in the form of carboxylate salts, to catalyze ring systems selectively to block copolymers and end-reactive polymers with controlled molecular weight through the control of catalyst concentration, reaction temperature, and reaction time. It is another object and advantage of the invention to increase by up to several orders of magnitude the reaction rates of the single reaction or the polymerization of ring systems with carboxylic acids, anhydrides, imides, lactones and carbonate esters, and to produce novel prepolymers, polymers, compositions, and compounds, including compounds of pharmaceutical use.

The invention comprises the use of $Cr^{+3}$ salts, e.g., chromium+3 carboxylate salts such as octoates, acetates, butyrates, benzoates, and the like, to enhance or accelerate the reaction of aziridines, oxetanes, thiiranes and oxiranes with carboxylic acids, anhydrides, imides, lactones and carbonate esters to form monomeric or polymeric reaction products. Equally important, chromium+3 carboxylate salts of the invention are used to enhance or accelerate the reaction of hydroxy compounds with anhydrides, lactones, and carbonate esters.

This invention is significant because it discloses the use of chromium+3 carboxylates to promote reactions of small ring systems and hydroxy compounds and finds unique application in the preparation and manufacture of non-polymeric chemicals, new plastic and polymeric materials as well as in improving the reaction or processing conditions of already existing non-polymeric, polymeric and plastic materials. A suitable $Cr^{+3}$ catalyst is HYCAT™ 2000, containing chromium+3 octoate, available from Dimension Technology Chemical Systems, Inc. of Fair Oaks, Calif.

One advantage of the $Cr^{+3}$ carboxylate catalysts of the invention over existing catalysts is that they do not promote homopolymerization of any of the reactants. The use of $Cr^{+3}$ catalysts results in the synthesis of block copolymers and end-reactive polymers with controlled molecular weight. By adjusting the concentration of the catalyst and reaction temperature, the reaction time can be accurately controlled. Another advantage is that the $Cr^{+3}$ catalysts of the present invention are remarkably universal. Use of a single $Cr^{+3}$ carboxylate results in copolymerization of the various reactants listed above. In contrast, metalloporphyrin catalysts are not universal; that is, different (e.g., Al, Zn) metalloporphyrins are needed to promote the reaction of different polymeric systems. Furthermore, in the case of the metalloporphyrins, usually a protic cocatalyst compound is needed to promote or initiate the reaction. This is not the case with the $Cr^{+3}$ catalysts of the present invention, in which no additional initiator or cocatalyst is required, although one could optionally be used.

In the chemical reaction systems of the invention, the $Cr^{+3}$ catalysts significantly increase the reaction rates. The overall reaction times are up to several orders of magnitude faster than existing catalyst systems, thereby significantly improving the process economics by providing considerable savings in labor and equipment productivity factors.

DETAILED DESCRIPTION OF THE BEST MODE FOR CARRYING OUT THE INVENTION

The following detailed description illustrates the invention by way of example, not by way of limitation of the principles of the invention. This description will clearly enable one skilled in the art to make and use the invention, and describes several embodiments, adaptations, variations, alternatives and uses of the invention, including what is presently believed to be the best mode of carrying out the invention.

The reactants are identified throughout by chemical nomenclature with reference to typical commercially available sources, by way of example and not by way of limitation. The reactants are also shown in structural format in the equations. It will be recognized by one skilled in the art that the reaction products may be single molecular species, or more complex mixtures of possible reaction products. Thus, while we have shown in the equations the structural formulas of reaction products, those are by way of example and not by way of limitation of the actual or possible products of the process using the $Cr^{+3}$ carboxylate catalysts with the reactants shown in the equation. Accordingly, the invention, without limitation, covers novel products of the inventive catalytic process.

A. Description of the Chromium+3 Carboxylate Catalyst

The catalyst of the present invention is a $Cr^{+3}$ salt. In one embodiment, the $Cr^{+3}$ salt is a $C_3$–$C_{60}$, straight or branch-chained, aryl, alkyl or aralkyl carboxylate. For purposes of this application, an "aryl" group is defined as being derived from an aromatic hydrocarbon typically with 6 to 20 carbon atoms, referably 6 to 16 carbon atoms, having a single ring (e.g., phenyl), or two or more condensed rings (e.g., naphthyl), or two or more aromatic rings which are linked by a single bond (e.g. biphenyl). The aryl group may optionally be mono-, di- or tri-substituted, independently, with lower branched or straight chain alkyl, lower cycloalkyl with 3 to 12 carbon atoms, lower branched or straight chain alkoxy, lower cycloalkoxy with 3 to 12 carbon atoms, fluoro, chloro, bromo, trifluoromethyl, cyano, nitro and/or difluoromethoxy, and so forth. The $Cr^{+3}$ carboxylate of the invention may optionally be a hexanoate, pentanoate, 2-ethylhexanoate, oleate, stearate, toluate, cresylate, benzoate, alkylbenzoate, alkoxybenzoate, napthanate, alkoxide, acetate, butyrate, propionate, octoate, and decanoate. In a preferred embodiment, the $Cr^{+3}$ salt is a $C_3$–$C_{10}$, straight or branch-chained, aryl, alkyl or aralkyl carboxylate, such as acetate, butyrate, propionate, benzoate, octoate, and decanoate. In a particularly preferred embodiment of the invention, the catalyst is chromium+3 octoate, where the octoate is a straight or branch-chained $C_8$, that may include either, or both, 2-ethyl-hexanoate or octanoate.

The catalyst can be used as a pure compound or may instead be used with a solvent or diluent, such as an alkyl ester of phthalic acid or a high boiling petroleum distillate. Thus the total chromium content in the catalyst employed will range from about 0.5 to the theoretical maximum for the pure carboxylate compound, e.g. about 10.8% for chromium+3 octoate. In a preferred embodiment, the $Cr^{+3}$ concentration in the chromium+3 octoate catalyst is from about 4% to about 8%, by weight. The catalyst/solvent system can range in viscosity from very fluid to very viscous.

The chromium+3 octoate catalyst can be prepared in accordance with Example 1 of U.S. Pat. No. 3,968,135, herein incorporated by reference. The preferred chromium+3 octoate concentration in the catalyst is 37.1% to 74.1%, with the balance, 25.9% to 62.9%, being composed of the solvent di-n-heptyl phthalate or a high-boiling petroleum distillate. The solvent in the chromium+3 octoate catalyst is present to aid in the handling of the catalyst, i.e., make it more fluid, dispersible, dispensable and contactible with the reactants in the reaction media and is not an essential component.

The preferred concentration of chromium in the total reaction media is from about 0.08% to about 2.0%, by weight, and more preferably from about 0.1% to about 0.7%, by weight, based on the combined weight of the reactants.

B. Use of Chromium+3 Carboxylate to Promote Aziridine Reactions

1. The Reaction of Aziridines with Carboxylic Acids are Accelerated with $Cr^{+3}$ Carboxylate Catalysts (a) Monomeric Systems: Reactions of Monofunctional Aziridines with Monofunctional Carboxylic Acids One embodiment of the present invention is shown in the following equation:

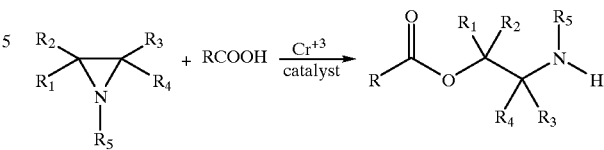

where $R_1$ through $R_5$ can be made up of any combination of hydrogen, alkyl, alkene, alkyne, aryl, alkylaryl, cyano, azido, carboxy, oxo, hydroxy, halo or like kind substituted groups and the monofunctional carboxylic acid can be any molecular weight and composition. The result of the reaction will be ring opening with any carboxylic acid to form single addition product esters with diverse functional groups.

One of ordinary skill in the art will recognize that the specific example, Example 1, provided below, demonstrates that chromium+3 carboxylates can catalyze the reaction between an aziridine and any carboxylic acid, regardless of whether the reactants are monofunctional or polyfunctional.

(b) Polymeric Systems: Reactions of Polyfunctional Aziridines with Polyfunctional Carboxylic Acids Another embodiment of the present invention is shown in the following equation:

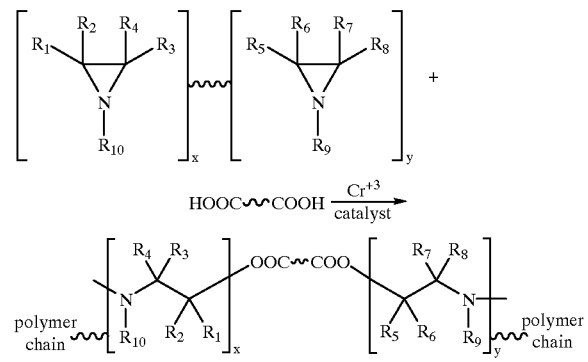

where $R_1$ through $R_{10}$ can be made up of any combination of hydrogen, alkyl, alkene, alkyne, aryl, alkylaryl, cyano, azido, carboxy, oxo, hydroxy, halo or like kind substituted groups and the polyfunctional carboxylic acid can be any molecular weight and composition provided that it contains at a minimum at least an average of 1.0 equivalents of the carboxylic acid group per mole and the aziridine combination, x and y are each at least 1, denoting a polyfunctional aziridine compound. The result of the reaction will be ring opening to form polyamine-esters containing diverse functional groups.

The following specific example illustrates one embodiment of chromium+3 catalysis of the reaction of an aziridine with a polyfunctional carboxylic acid:

EXAMPLE 1

Reaction of pentaerythritol-tris-B-(N-aziridinyl)-propionate with a Dimer Acid

Into a mixing cup (Paul N. Garner, 95 mm diameter×47 mm deep) was weighed 15.5 grams (100.3 meq) of pentaerythritol-tris-B-(N-aziridinyl)-propionate (commercially available as Xama-7™ from EIT, Inc.), 27.7 grams (101.6 meq) of a dimer acid (commerically available as Empol® 1016 dimer acid from Henkel Corporation), and 4.28 grams (0.5% $Cr^{+3}$ based on the weight of the reactants) of the $Cr^{+3}$ of the invention and mixed for 2 minutes with a spatula, then placed in a Garner wire-stirred standard gel timer (Model GT-S) at 32° C. After 1 minute of stirring, the contents of the cup were completely solidified into a hard rubbery mass.

As a control, the identical reaction was also performed without the use of the chromium catalyst. Into an aluminum weighing dish (Whatman No. 8283, 60 mm diameter×13 mm deep) was weighed 1.6 grams (10.36 meq) of pentaerythritol-tris-B-(N-aziridinyl)-propionate and 2.7 grams (9.90 meq) of dimer acid and mixed for 2 minutes with a spatula, then allowed to stand at 32° C. overnight. The composition was tacky after 15 minutes and solidified into a semi-tacky mass in about 24 hours.

2. The Reaction of Aziridines with Anhydrides is Accelerated with the $Cr^{+3}$ Carboxylate Catalyst One embodiment of the present invention is shown in the following equation:

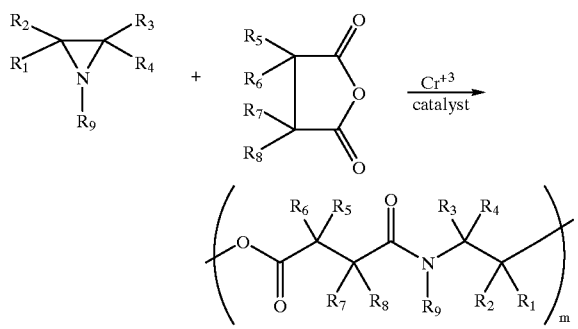

where $R_1$ through $R_9$ can be made up of any combination of hydrogen, alkyl, alkene, alkyne, aryl, alkylaryl, cyano, azido, carboxy, oxo, hydroxy, halo or like kind substituted groups and m is at least 1. The result of the reaction will be the ring opening of the aziridine with an anhydride, thereby forming an ester-amide polymer.

The following specific example illustrates one embodiment of these reactions of aziridines with anhydrides in the presence of the $Cr^{+3}$ carboxylate catalyst:

EXAMPLE 2

Reaction of pentaerythritol-tris-B-(N-aziridinyl)-propionate with methyl Hexahydrophthalic Anhydride (MHHPA)

MHHPA, 4.3 g (51.1 meq) and pentaerythritol-tris-B-(N-aziridinyl)-propionate (identified in Example 1, above), 2.5 g (17.6 meq) were weighed into a 30 ml beaker and thoroughly mixed. A small sample, 0.6 g, was transferred into a 15 ml beaker for a control. To the larger portion, 6.2 g, was added 0.2 g (0.26% Cr based on the weight of the reactants) of the $Cr^{+3}$ catalyst. The contents of both flasks were allowed to react at room temperature, 22° C. After a 10 minute reaction period the chromium catalyzed material was no longer mobile when the beaker was tipped on its side. The material in the control beaker was still mobile. After a 25 minute reaction period the control reaction was not mobile. Although the chromium catalyzed reaction was complete at least twice as fast as the control reaction, both the control and chromium catalyzed reaction products showed an equal amount of hardness when prodded with a pointed spatula. Both reaction products were insoluble in acetone.

EXAMPLE 3

Reaction of pentaerythritol-tris-B-(N-aziridinyl)-propionate with bicyclo (2.2.2) oct-7-ene-2,3,5,6-tetracarboxylic dianhydride (BTA)

Into an aluminum weighing pan was put 6.6 g (53.2 meq) of BTA, 7.7 g (54.1 meq) of pentaerythritol-tris-B-(N-aziridinyl)-propionate (identified in Example 1, above) and 0.4 g of the $Cr^{+3}$ catalyst (0.1 wt % chromium based on the weight of the reactants). After 45 minutes at 41° C. the contents of the pan cured to a hard, brittle olive green solid.

It will be evident to one of ordinary skill in the art that Example 2 and 2b, above, also provides evidence that the $Cr^{+3}$ catalyst of the invention can be used to accelerate the reaction of polyfunctional aziridines and/or anhydrides, as well as that of monofunctional reactants.

3. Aziridines are not Homopolymerized by the $Cr^{+3}$ Carboxylate Catalyst

The following specific example demonstrates that the $Cr^{+3}$ carboxylate catalyst of the invention does not promote the homopolymerization of aziridines:

EXAMPLE 4

Attempted Homopolymerization of pentaerythritol-tris-B-(N-aziridinyl)-propionate with $Cr^{+3}$ Catalyst To show that pentaerythritol-tris-B-(N-aziridinyl)-propionate (identified in Example 1, above) does not homopolymerize in the presence of $Cr^{+3}$ catalyst at elevated temperature, 6.8 grams of pentaerythritol-tris-B-(N-aziridinyl)-propionate and 0.4 g of the $Cr^{+3}$ catalyst (0.3% chromium based on the weight of pentaerythritol-tris-B-(N-aziridinyl)-propionate) was placed into an aluminum weighting pan and heated to 41° C. for 3 hours and 15 minutes then allowed to stand at 16 to 21° C. for 9 days at which time the contents of the pan was still liquid.

C. Use of Chromium+3 Carboxylate to Promote Oxetane Reactions

1. The Reaction of Oxetanes with Anhydrides is Accelerated with $Cr^{+3}$ Carboxylate Catalysts In one embodiment, the present invention provides for the following reaction:

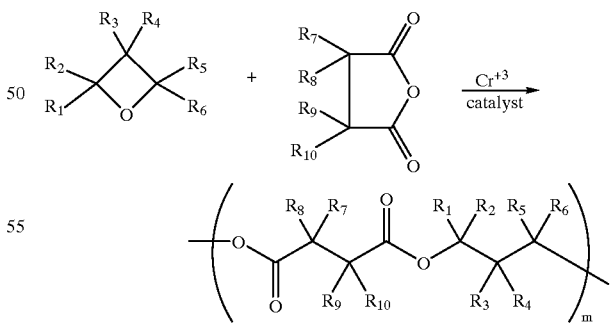

where $R_1$ through $R_{10}$ can be made up of any combination of hydrogen, alkyl, alkene, alkyne, aryl, alkylaryl, cyano, azido, carboxy, oxo, hydroxy, halo or like kind substituted groups and m is at least 1. The result of the reaction will be polyesters with or without pendant hydroxyl or carboxylic acid groups depending on the mole ratio of the oxetane to anhydride employed.

The following specific example illustrates one embodiment of $Cr^{+3}$ catalysis of the reaction of oxetanes with anhydrides.

EXAMPLE 5

Reaction of 3-bromomethyl, 3-methyloxetane (BMMO) with Methyl Hexahydrophthalic Anhydride (MHHPA)

MHHPA, 2.6 g (15.5 mmol) and BMMO, 2.5 g (15.1 mmol. 3% excess) were weighed into a 50 ml Erlenmeyer flask and thoroughly mixed. A small sample. 1.0 g was transferred into a 25 ml Erlenmeyer flask for a control. To the larger portion. 4.1 g, was added 0.3 g (0.6% Cr based on the weight of the reactants) of the $Cr^{+3}$ catalyst The contents of both flasks were simultaneously heated to 95 to 100° C. in a hot oil bath for a period of 1½ hours. Samples were periodically taken from each flask for FTIR analysis. After a 30 minute reaction period, a new, very strong ester carbonyl peak was observed in the chromium catalyzed reaction at 1734 $cm^{-1}$ along with the anhydride carbonyl peaks at 1861 $cm^{-1}$ and 1787 $cm^{-1}$. Because the chromium catalyzed material would immediately solidify when removed from the reaction flask, additional samples could not be taken for FTIR analysis. On completion of the reaction, when the chromium catalyzed reaction product was cooled to room temperature, a hard polymer formed. Conversely, the control samples remained liquid though out the reaction period and upon cooling to room temperature. FTIR analysis of the control material showed no apparent change in chemical composition during the heating period. Titration with sodium hydroxide of a sample of the chromium catalyzed reaction mixture showed this material contained 2.58 mmol of unreacted MHHPA. The amount of MHHPA that was converted to product in the chromium catalyzed reaction was 81.9%.

It will be evident to one of ordinary skill in the art that Example 5. above, demonstrates that the $Cr^{+3}$ catalyst of the invention can also he used to accelerate the reactions of both monofunctional and polyfunctional oxetanes and anhydrides.

2. Importance of the $Cr^{+3}$ Carboxylate Catalyst in the Reaction of Oxetanes with Anhydrides a Comparison with other Metal Carboxylate Catalysts To show the importance of using the $Cr^{+3}$ carboxylate catalysts, other metal carboxylates, such as cobalt octoate and nickel octoate, were used in an attempt to accelerate the oxetane reaction with an anhydride. Neither cobalt nor nickel carboxylates were found to be useful in promoting these reactions.

EXAMPLE 6

Attempted Reaction of Methyl Hexahydrophthalic Anhydride (MHHPA) with 3-bromomethyl-3-methyl-oxetane (BMMO) Catalyzed by the Cobalt Salt of 2-ethylhexanoic Acid MHHPA, 3.4 g (20.2 mmol) and BMMO 3.3 g (20.0 mmol) were weighed into a 50 ml Erlenmeyer flask and 0.55 g, (0.5% Co based on the weight of the reactants) of the cobalt octoate catalyst was added and thoroughly mixed. The flask was heated to 100±2° C. in a hot oil bath for a period of two hours and 10 minutes. Samples were periodically taken from the flask for FTIR analysis. The reaction was followed by observing the change in the absorption ratio of the anhydride carbonyl groups (1861 and 1787 $cm^{-1}$) converting to an ester carbonyl at 1731 $cm^{-1}$. Only a slight ester carbonyl absorption at $1731^{-1}$ cm was detected at the end of the reaction. These data show that $Co^{+3}$, in the presence of the 2-ethylhexanoate anion, does not accelerate the reaction of BMMO with MHHPA.

EXAMPLE 7

Attempted Reaction of Methyl Hexahydro Phthalic Anhydride (MHHPA) with 3-bromomethyl-3-methyl-oxetane (BMMO) Catalyzed by the Nickel Salt of 2-ethylhexanoic Acid MHHPA, 3.4 g (20.2 mmol) and BMMO 3.4 g (20.6 mmol) were weighed into a 50 ml Erlenmeyer flask and 0.45 g, (0.5% Ni based on the weight of the reactants) of the nickel octoate catalyst was added and thoroughly mixed. The flask was heated to 100±2° C. in a hot oil bath for a period of 1.75 hours. Samples were periodically taken from the flask for FTIR analysis. The reaction was followed by observing the change in the absorption ratio of the anhydride carbonyl groups (1861 and 1787 $cm^{-1}$) converting to an ester carbonyl at 1731 $cm^{-1}$. A gelatinous material formed during the reaction, which liquefied on standing at room temperature for 24 hours. Only a slight ester carbonyl absorption at 1731 $cm^{-1}$ was detected at the end of the reaction. Based on the titration of the reaction product, nearly all, 99.4%, of the MHHPA was recovered. These data show that $Ni^{+2}$, in the presence of the 2-ethyl hexanoate anion, does not accelerate the reaction of BMMO with MHHPA.

3. The Reaction of Oxetanes with Carboxylic Acids is Accelerated with $Cr^{+3}$ Carboxylate Catalysts (a) Monomeric Systems: Reactions of Oxetanes with Monofunctional Carboxylic Acids.

One embodiment of the invention is shown by the following equation:

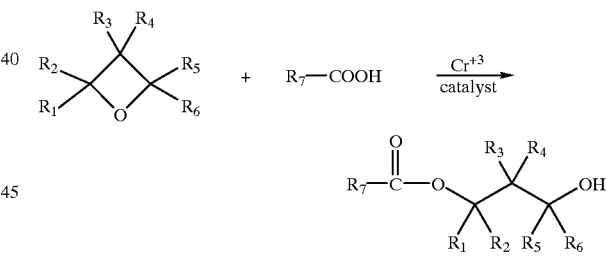

where R through $R_7$ can be made up of any combination of hydrogen, alkyl, alkene, alkyne, aryl, alkylaryl, cyano, azido, carboxy, oxo, hydroxy, halo or like kind substituted groups. The products of the reaction are gamma-terminated hydroxy esters.

The following specific examples illustrates one embodiment of the reaction of oxetanes with monofunctional carboxylic acids:

EXAMPLE 8

Reaction of 3-bromomethyl, 3-methyl-oxetane (BMMO) with 2-ethylhexanoic Acid BMMO, 3.3 g (20.0 mmol) and 2-ethylhexanoic acid. 2.9 g (20.1 mmol) were weighed into a 50 ml Erlenmeyer flask and a 0.8 g portion was transferred into a 25 ml Erlenmeyer flask to serve as a control. To the major portion, 5.4 g, was added 0.3 g (0.4% Cr based on the weight of the reactants)

of the $Cr^{+3}$ catalyst and thoroughly mixed. Both flasks were heated to 74 to 77° C. in a hot oil bath for a period of 5 hours and 20 minutes. Samples were periodically taken from both flasks for FTIR analysis. The reaction was followed by observing the change in the absorption ratio of the acid carbonyl (1701 $cm^{-1}$) converting to an ester carbonyl (1735 $cm^{-1}$) and the formation of a hydroxyl group (3450 $cm^{-1}$) due to opening of the oxetane ring as the reaction proceeded. The relative reaction rate was determined by following the ratio of the ester carbonyl absorption peak to the acid carbonyl absorption peak in the control and the chromium catalyzed reactions. In the control reaction the ratio of the ester carbonyl to the acid carbonyl increased from 0.57:1.0 to 0.70:1.0, respectively, in 320 minutes. In the chromium catalyzed reaction the ratio of the ester carbonyl to the acid carbonyl increased from 0.60:1.0 to 1.27:1.0 in 315 minutes. Comparatively, the chromium catalyzed reaction was 73 times faster than the control reaction. The amount of unreacted 2-ethylhexanoic acid was determined (5.66 mmol) in the chromium catalyzed reaction product by titration with 0.0974 N sodium hydroxide and showed an overall conversion of 68.4%.

EXAMPLE 9

Reaction of 3-bromomethyl 3-methyl-oxetane (BMMO) with Benzoic Acid

BMMO. 3.5 g (21.2 mmol) and benzoic acid, 2.4 g (i (19.7 mmol) were weighed into a 50 ml Erlenmeyer flask and 2.0 g, (2.7% Cr based on the weight of the reactants) of the $Cr^{+3}$ catalyst was added and thoroughly mixed. The flask was heated to 97 to 100° C. in a hot oil bath for a period of 4 hours. Samples were periodically taken from the flask for FTIR analysis. The reaction was followed by observing the change in the absorption ratio of the acid carbonyl (1700 $cm^{-1}$) converting to an ester carbonyl (1723 $cm^{-1}$) and the formation of a hydroxyl group (3447 $cm^{-1}$) due to opening of the oxetane ring as the reaction proceeded. The reaction was considered complete when the acid carbonyl absorption peak could no longer be seen. The amount of unreacted benzoic acid was determined (5.3 mmol) by titration with 0.0974 N sodium hydroxide and showed an overall conversion of 84.6%.

(b) Polymeric Systems: Reactions of Oxetanes with Polyfunctional Carboxylic Acids Another embodiment of the invention is shown by the following equation:

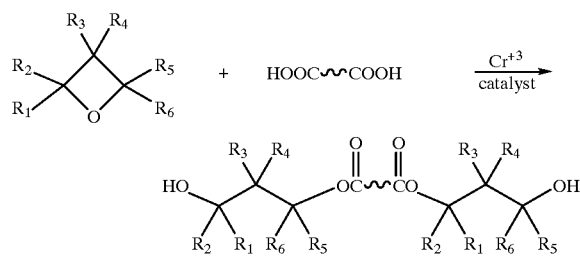

where $R_1$ through $R_6$ can be made up of any combination of hydrogen, alkyl, alkene, alkyne, aryl, alkylaryl, cyano, azido, carboxy, oxo, hydroxy, halo or like kind substituted groups. The products of the reaction are polymeric esters with pendent hydroxyl groups.

The following specific examples illustrate one embodiment of the $Cr^{+3}$-catalyzed reaction of oxetanes with polyfunctional carboxylic acids:

EXAMPLE 10

Reaction of 3-bromomethyl-3-methyloxetane (BMMO) with a Dimer Acid 4.8 g (8 mmol) of the dimer acid used in Example 1, 2.9 g (17.6 mmol, 10% excess) of BMMO and 1.1 g (1.1% Cr based on the weight of the reactants) of the $Cr^{+3}$ catalyst were weighed into a 50 ml Erlenmeyer flask and the solution heated to 96 to 98° C. in a hot oil bath for a period of 6⅓ hours. Samples were periodically taken for FTIR analysis. The reaction was followed by observing the change in the absorption ratio of the acid carbonyl (1710 $cm^{-1}$) converting to an ester carbonyl (1738 $cm^{-1}$) and the formation of a hydroxyl group (3444 $cm^{-1}$) due to opening of the oxetane ring as the reaction proceeded. After one hour, the absorption of the acid carbonyl was very slight and appeared as a shoulder on the ester carbonyl peak and could not be measured and the hydroxyl absorption was at its maximum. Both of these observations showed the reaction was complete. The reaction was heated for an additional 5⅓ hours to see if any additional changes could be seen in the carbonyl region of the FMIR spectra. None were observed, indicating that the reaction had proceeded to completion within the first hour.

EXAMPLE 11

Reaction of 3-bromomethyl-3-methyloxetane (BMMO) with Dimer Acid 2.8 g (4.7 mmol) of the dimer acid identified in Example 1, above, and 1.6 g (9.7 mmol, 3% excess) of BMMO were weighed into a 50 ml Erlenmeyer flask and thoroughly mixed. A small sample, 0.8 g was transferred into a 25 ml Erlenmeyer flask for a control. To the larger portion was added 0.4 g (0.9% Cr based on the weight of the reactants) of the $Cr^{+3}$ catalyst. The contents of both flasks were simultaneously heated to 95 to 106° C. in a hot oil bath for a period of 5 hours. Samples were periodically taken for FRIR analysis. The reaction was followed by observing the change in the absorption ratio of the acid carbonyl (1710 $cm^{-1}$) converting to an ester carbonyl (1738 $cm^{-1}$) and the formation of a hydroxyl group (3444 $cm^{-1}$) due to opening of the oxetane ring as the reaction proceeded. After 5 hours, analysis of the control sample showed that no hydroxyl group was formed and the ester carbonyl absorption peak was only a slight blip (that could not be measured) on the shoulder of the acid carbonyl absorption peak. However, the sample with the chromium catalyst showed the reaction was complete after 2½ hours of reaction. Both of these observations showed that the $Cr^{+3}$ carboxylate catalyzed the reaction of the oxetane with the carboxylic acid, as compared to the uncatalyzed reaction.

(c) Polymeric Systems: Reaction of Polyfunctional Oxetanes with Carboxylic Acids Based on the evidence given in Examples 8, 9, 10, and 11, above, it will be evident to one of ordinary skill in the art that the reaction of di- or poly-functional oxetanes with di- or polyfunctional carboxylic acids will produce new and useful polymers with pendent hydroxy or carboxylic groups depending on the mole ratio of the oxetanes and carboxylic acids employed. Accordingly, the present invention also provides for the reaction shown in the following equation.

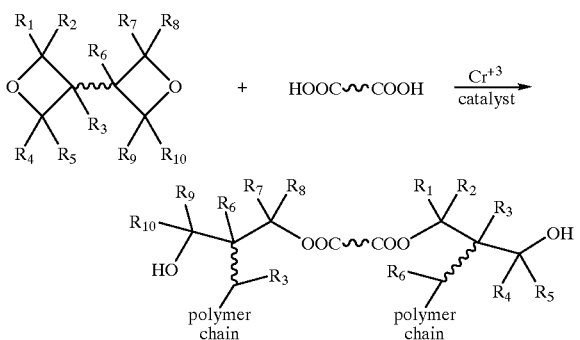

where $R_1$ through $R_{10}$ can be made up of any combination of hydrogen, alkyl, alkene, alkyne, aryl, alkylaryl, cyano, azido, carboxy, oxo, hydroxy, halo or like kind substituted groups and the polyfunctional carboxylic acid can be any molecular weight and composition provided that it contains at a minimum at least an average of 1.0 equivalent of carboxylic acid group per mole. The result of the reaction are polyesters, polyols, and/or carboxylic acids.

4. The Reaction of Oxetanes with Imides is Accelerated with $Cr^{+3}$ Carboxylate Catalysts Another example of the catalyst of the invention is illustrated in the following reaction:

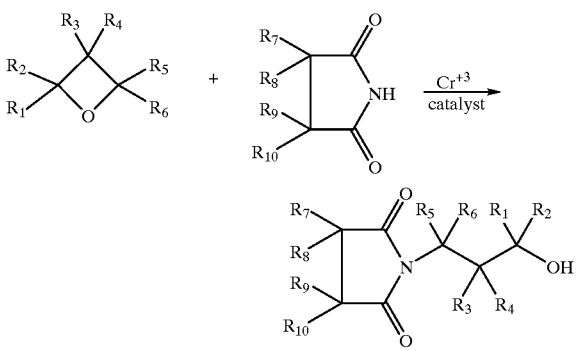

where $R_1$ through $R_{10}$ can be made up of any combination of hydrogen, alkyl, alkene, alkyne, aryl, alkylaryl, cyano, azido, carboxy, oxo, hydroxy, halo or like kind substituted groups. One of ordinary skill in the art will readily recognize that the result of the reaction will be a gamma-hydroxy terminated imide.

EXAMPLE 12

Reaction of 3-bromomethyl-3-methyloxetane (BMMO) with Succinimide

Succinimide. 2.9 g (29.3 mmol) and BMMO, 4.7 g (28.5 mmol) and 10 ml of 2-methyltetrahydrofuran (solvent) and 0.8 g (0.8% Cr based on the weight of the reactants) of the activated $Cr^{+3}$ catalyst was put into a 50 ml Erlenmeyer flask and thoroughly mixed. The slurry was heated to 65 to 70° C. in a hot oil bath for a period of 1 hour and 55 minutes. Samples were periodically taken from the flask for FTIR analysis. After 10 minutes about 50% of the solids were dissolved; after 50 minutes about 90% of the solids were dissolved and after 1 hour and 45 minutes all of the solids were dissolved. During this time a new, very strong carbonyl peak was observed being formed at 1709 $cm^{-1}$ and the appearance of a hydroxyl group was also observed at 3461 $cm^{-1}$. The reaction mixture was allowed to cool to room temperature and about 0.3 grams of solids were removed by filtration and air dried (mp 115 to 122° C.; succinimide mp: 123–125° C.). The filtrate was concentrated in vacuo first at water aspirator vacuum at 72° C. then at vacuum pump pressure and 65 to 70° C. The weight of the concentrate was 6.9 grams. The concentrate was loaded onto a chromatography column (5 inch long by ½ inch diameter) containing chromatography grade alumina and then eluted first with 40 ml of methylene chloride followed by 50 ml of methanol. Both eluents were concentrated in vacuo as before. The methylene chloride eluent concentrate was a liquid and weighed 4.8 grams (64% yield). The methanol eluent concentrate, 1.5 grams (20% crude yield) was a pasty solid but had an IR spectra very similar to the product recovered from the methylene chloride eluent concentrate.

It will be evident to one of ordinary skill in the art that Example 12, above, demonstrates that the $Cr^{-3}$ catalyst of the invention can not only be used to accelerate the reactions of monofunctional oxetanes and imides, but of polyfunctional oxetanes and imides as well.

D. Use of Chromium +3 Carboxylate to Promote Hydroxy Compound Reactions

1. The Reaction of Hydroxy Compounds with Anhydrides is Accelerated with $Cr^{+3}$ Carboxylate Catalysts This embodiment of the invention is shown in the following equations.

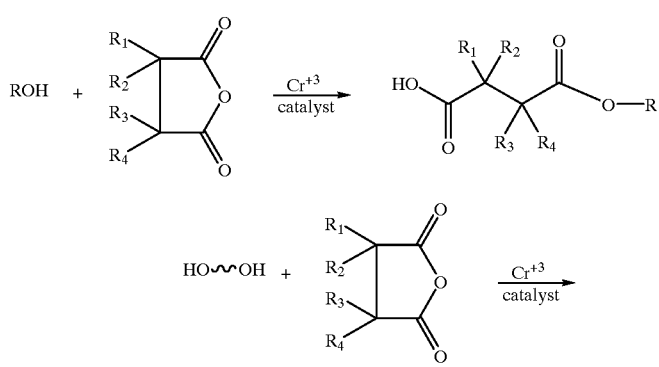

-continued

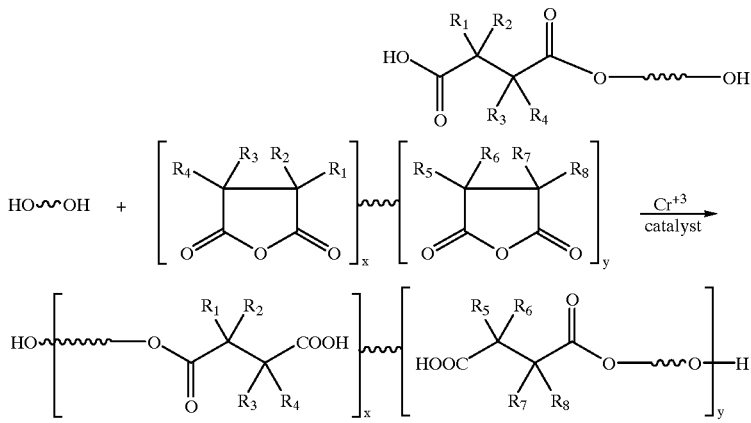

where R through $R_8$ can be made up of any combination of hydrogen, alkyl, alkene, alkyne, aryl, alkylaryl, cyano, azido, carboxy, oxo, hydroxy, halo or like kind substituted groups and where x and y are each at least 1, denoting a polyfunctional anhydride compound of any composition and molecular weight and the hydroxyl group can be in the form of a mono to polyfunctional hydroxy compound of any composition and molecular weight. The products of the reaction are either non-polymeric or polymeric esters with pendent hydroxyl or carboxylic acid groups depending on the mole ratio of the reactants. The following specific examples illustrate the ability of $Cr^{+3}$ carboxylate to promote hydroxy compound reactions under different conditions:

EXAMPLE 13

Reaction of Methyl Hexahydrophthalic Anhydride (MHHPA) with a Dihydroxy Ester Resin MHHPA, 33.6 g (199.8 mmol), a dihydroxy ester resin (commercially available as Formrez® 11–112 from Witco Corp.), 100.6 g (200.0 meq) and 8.5 g of the $Cr^{+3}$ catalyst (0.5 wt % chromium based on the weight of the reactants) were weighed into a 250 ml Erlenmeyer flask and thoroughly mixed. The sample was heated to 75±3° C. in a water bath for 6 hours and 10 minutes. Samples were periodically taken for FTIR analysis. The reaction was followed by observing the change in the absorption ratio of the anhydride carbonyl groups (1788 $cm^{-1}$ and 1857 $cm^{-1}$) converting to an ester carbonyl group (1734 $cm^{-1}$). The intensity of these peaks were compared to an absorption peak, at 1454 cm–1 that appeared to remain constant throughout the reaction. After 4 hours the anhydride carbonyl absorption peak (1788 $cm^{-1}$) was only a slight blip on the shoulder of the ester carbonyl absorption peak. Two hours later, no anhydride carbonyl peak absorption could be detected. The ratio of the "constant" peak to the anhydride peak (1788 $cm^{-1}$) increased from 0.44:1.0 to >128:1.0, respectively, in 250 minutes. In a control run, where no chromium catalyst was used, 10.2 g (20.3 mmol) of the dihydroxy ester resin and 3.5 g (20.8 mmol) MHHPA were reacted at 74 to 85° C. Even though the control run was conducted at a higher average reaction temperature than the experiment containing the chromium catalyst, the rate of increase of the "constant" peak to the anhydride peak was significantly lower, going from 0.44:1.0 to 0.93:1.0, respectively, in 263 minutes. Comparatively, the chromium catalyzed reaction was 138 times faster than the control run. A sample, 0.6625 g, of the reaction product in the chromium-catalyzed reaction was titrated to the end point with 9.76 ml (950.6 mmol) 0.0974 N sodium hydroxide. Based on this titration, the total acid content in the reaction product is 204.7 mmol. This corresponds to a 98.8% conversion of the MHHPA to the product. These observations showed that the $Cr^{+3}$ catalyst accelerated the reaction of the anhydride with the difunctional hydroxy compound.

EXAMPLE 14

Reaction of Methyl Hexahydrophthalic Anhydride (MHHPA) with a Dihydroxy Ester Resin 3.4 g (20.2 mmol) of MHHPA and, 10.2 g (10.1 mmol) of the dihydroxy ester resin identified in Example 13, above, were weighed into a 50 ml Erlenmeyer flask and 1 .2 g, (0.7% Cr based on the weight of the reactants) of the $Cr^{+3}$ catalyst was added and thoroughly mixed. The flask was heated to 99±1° C. in a hot oil bath for a period of 2.5 hours. Samples were periodically taken from the flask for FTIR analysis. The reaction was followed by observing the change in the absorption ratio of the anhydride carbonyl groups (1857 and 1788 $cm^{-1}$) converting to an ester carbonyl (1734 $cm^{-1}$). The reaction was considered complete when the anhydride carbonyl absorption peak was just a small shoulder on the ester peak. The reaction product was titrated with 0.0974 N sodium hydroxide and showed an overall conversion of 93.9%.

EXAMPLE 15

Reaction of a Copolymer of Maleic Anhydride and Styrene with a Dihydroxy Ester Resin Into an aluminum weighing pan was placed 3.7 g (26.7 mmol anhydride) of a copolymer of maleic anhydride and styrene (commercially available as Scripset® 520 from Monsanto Company), 6.6 g (13.1 meq) of the dihydroxy ester (used and identified in Example 13) and 0.3 g (0.15% Cr based on the weight of the reactants) of the $Cr^{+1}$ catalyst and heated to 54 to 60° C. for a period of 5 hours during which time a flexible polymer was formed. The pan was heated for an additional 12.5 hours at 54° C. but no change in the consistency of the very elastic polymer was observed. After storing the polymer at room temperature for 10 months no change in the polymer appearance, including no shrinkage, was observed.

In a separate control run without using the chromium catalyst, 2.5 g (18.1 mmol anhydride) of the maleic anhydride/styrene copolymer was mixed with 4.6 g (9.1 meq) dihydroxy ester and heated to 57° C. for 20 hours. After 1¼ hours a gel started to form that was very sticky and not elastic in comparison to the polymer made with the chromium catalyst. After 20 hours the reactants were completely polymerized but the polymer remained very sticky. After storage at room temperature for 10 months the polymer remained sticky and there appeared to be some shrinkage.

2. The Reaction of Hydroxy Compounds with Lactones is Accelerated with $Cr^{+3}$ Carboxylate Catalysts Another embodiment of the present invention is shown in the following equations:

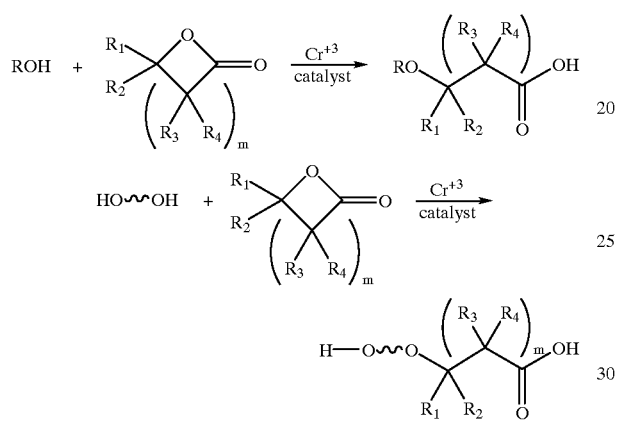

where R through $R_4$ can be made up of any combination of hydrogen, alkyl, alkene, alkyne, aryl, alkylaryl, cyano, azido, carboxy, oxo, hydroxy, halo or like kind substituted groups and the hydroxy compound can be any molecular weight and composition provided that it contains at a minimum at least an average of 1.0 equivalents of hydroxyl group per mole and m is at least 1, representing at least one carbon in the lactone ring. The result will be reaction of lactones with single or polyhydroxy compounds forming monomer or polyether-esters, Based on the evidence given in Examples 13, 14, and 15. above, and Example 16, below, it appears that $Cr^{+3}$ carboxylate will accelerate the reaction of lactones with hydroxy compounds.

3. The Reactions of Hydroxy Compounds with Carbonate Esters is Accelerated with $Cr^{+3}$ Carboxylate Catalysts Another embodiment of the present invention is shown in the following equation:

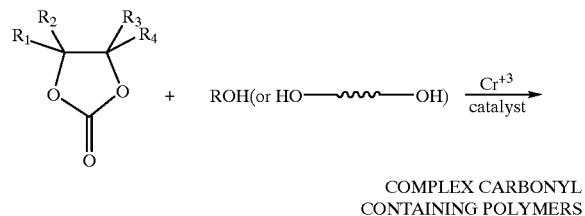

COMPLEX CARBONYL CONTAINING POLYMERS where R through $R_4$ can be made up of any combination of hydrogen, alkyl, alkene, alkyne, aryl, alkylaryl, cyano, azido, carboxy, oxo, hydroxy, halo or like kind substituted groups and the hydroxy compound can be any molecular weight and composition provided that it contains at a minimum at least an average of 1.0 equivalents of hydroxyl group per mole. The result of the reaction will be a complex monomer or polymer ether ester.

Based on the evidence given in Examples 13, 14 and 15. above, and Example 17, below, it appears that $Cr^{+3}$ carboxylate will accelerate the reaction of carbonate esters with hydroxy compounds.

E. The Use of Chromium+3 Carboxylate to Promote Other Ring Reactions

1. $Cr^{+3}$ Carboxylates Accelerate the Reaction of Lactones with Oxiranes and Aziridines Still another embodiment of the present invention is illustrated by the following equation:

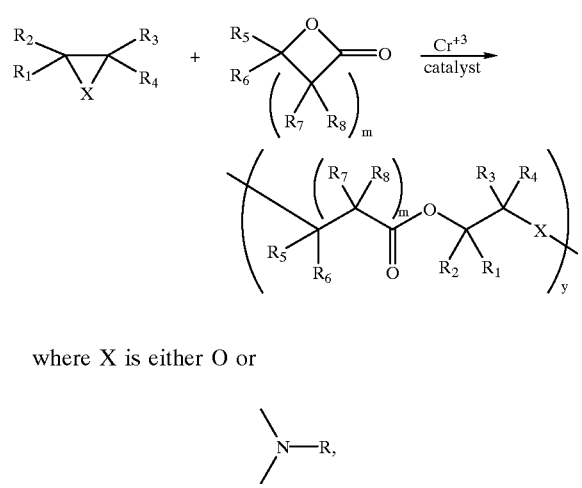

where X is either O or

\
 N—R,
/ and where R through $R_8$ can be made up of any combination of hydrogen, alkyl, alkene, alkyne, aryl, alkylaryl, cyano, azido, carboxy, oxo, hydroxy, halo or like kind substituted groups and m is at least 1, representing at least one carbon in the lactone ring, and y is at least 1.

The following specific example illustrates one embodiment of this reaction:

EXAMPLE 16

Reaction of gamma-butyrolactone with 3.4-epoxycyclohexylmethyl-3,4epoxy-cyclohexylcarboxylate Gamma butyrolactone, 3.2 g (37.2 mmol) and 3.4-epoxycyclohexylmethyl-3,4-epoxy-cyclohexylcarboxylate (commerically available as ERL 4221 from Union Carbide Corp.), 5.4 g (21.4 mmol) were weighed into a 50 ml Erlenmeyer flask and thoroughly mixed. A portion, 2.2 g, was transferred into a 25 ml Erlenmeyer flask for a control. To the remainder, 6.4 g, was added 0.25 g (0.3% Cr based on the weight of the reactants) of the $Cr^{+3}$ catalyst. The contents of both flasks were simultaneously heated to 97 to 100° C. in a hot oil bath for a period of 3 hours. Samples were periodically taken over the 3 hour reaction period from the "control flask" for FTIR analysis. Because the reactants containing the chromium catalyst polymerized into a resinous, rubbery solid mass after one hour of reaction, only one liquid sample could be taken 35 minutes after the reaction was started. While the absorption ratio of the ester peaks at 1773 $cm^{-1}$ and 1729 $cm^{-1}$ remained fairly constant, varying between 1.4:1.0 to 1.1: 1.0, respectively, in the control run, the ratio in the only sample taken from the chromium catalyzed reaction before it polymerized into a solid mass was 4.6:1.0, showing the rapid formation of a new ester group. In contrast, the end of the three hour reaction time, the control sample was still liquid.

To see if the butyrolactone, alone, could be polymerized by the chromium catalyst, in a separate test, 4.0 g of gamma butyrolactone was mixed with 0.5 g of the $Cr^{+3}$ catalyst (1.0% of the butyrolactone weight) and heated to 99° C. for 4 hours. No polymerization occurred. The sample remained liquid.

All of these observations show that the $Cr^{+3}$ catalyst accelerates the reaction and polymerization of gamma butyrolactone with 3,4-epoxycyclohexylmethyl-3,4-epoxy-cyclohexylcarboxylate, without catalyzing homopolymerization of the gamma-butyrolactone.

It will be recognized by one of ordinary skill in the art that Example 16, above, and Examples 17 and 18, below, indicate that it appears that the $Cr^{+3}$ carboxylate catalyst of the invention will accelerate the reaction between lactones and aziridines, as it accelerates the reaction between lactones and oxiranes. In such catalyzed reactions, the lactone, aziridine, and/or oxirane optionally can be polyfunctional.

2. $Cr^{+3}$ Carboxylate Accelerates the Reaction of Carbonate Esters with Oxiranes and Aziridines An alternative embodiment of the invention is illustrated by the following equation:

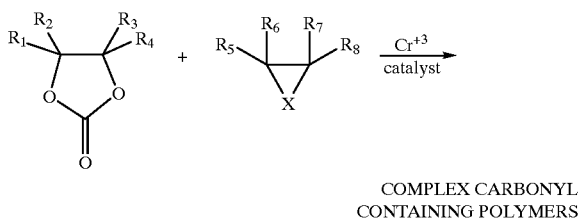

COMPLEX CARBONYL CONTAINING POLYMERS where X is either O and,

and where R through $R_8$ can be made up of any combination of hydrogen, alkyl, alkene, alkyne, aryl, alkylaryl, cyano, azido, carboxy, oxo, hydroxy, halo or like kind substituted groups and the carbonate ester can be any molecular weight and composition, and the complex polymer that is formed represents, at a minimum, the reaction of one-mole of the three member ring with one-mole of the carbonate ester. The result of the reaction is a complex polymer.

One of ordinary skill in the art will readily recongize that each of the reactants of the catalyzed reaction can be either monofunctional or polyfunctional.

The following specific example illustrates one embodiment of this reaction:

EXAMPLE 17

Reaction of Propylene Carbonate with 3,4-epoxycyclohexylmethyl-3,4-epoxy-cyclohexylcarboxylate Propylene carbonate, 2.1 g (20.4 mmol), and 3,4-epoxycyclohexylmethyl-3,4-epoxy-cyclohexylcarboxylate (identified in Example 16, above), 2.8 g (20.4 mmol), were weighed into a 50 ml Erlenmeyer flask and thoroughly mixed. A portion, 1.0 g, was transferred into a 25 ml Erlenmeyer flask for a control. To the remainder, 3.9 g, was added 0.2 g (0.4% Cr based on the weight of the reactants) of the $Cr^{+3}$ catalyst. The contents of both flasks were simultaneously heated to 75 to 94° C. in a hot oil bath for a period of 3 hours. Samples were periodically taken over the 3 hour reaction period from the "control flask" for FTIR analysis. Because the reactants containing the chromium catalyst polymerized into a resinous. rubbery solid mass after 40 minutes of reaction, only two liquid sample could be taken after the reaction was started. While the absorption ratio of the ester peaks at 1796 $cm^{-1}$ and 1729 $cm^{-1}$ remained constant at 1.2:1.0, respectively, in the control run, and was slightly higher (1.4–1.6:1.0, respectively) in the two samples taken from the chromium catalyzed reaction, at the end of the three hour reaction time, the control sample was still liquid at the end of the reaction.

To see if the propylene carbonate, alone, could be polymerized by the chromium catalyst, in a separate test, 2.3 g of propylene carbonate was mixed with 0.25 g of the $Cr^{+3}$ catalyst (0.9% of the propylene carbonate weight) and heated to 98° C. for 3 hours and 20 minutes. No polymerization occurred. The sample remained liquid.

All of these observations show that the $Cr^{+3}$ catalyst accelerates the reaction and polymerization of propylene carbonate with 3.4-epoxycyclohexylmethyl-3,4-epoxy-cyclohexylcarboxylate.

EXAMPLE 18

Reaction of Propylene Carbonate with pentaerythritol-tris-B-(N-aziridinyl)-propionate Into an aluminum weighing pan was put propylene carbonate, 2.2 g (21.5 mmol), pentaerythritol-tris-B-(N-aziridinyl)-propionate (as identified in Example 1, above), 3.1 g (7.3 mmol) and 1.0 g of the $Cr^{+3}$ catalyst (0.9 wt % chromium based on the weight of the reactants). The pan was allowed to stand at room temperature, 18° C., for 24 hours, during which time, the contents of the pan polymerized into a solid that was easily pulverized into a powder.

3. $Cr^{+3}$ Carboxylates Accelerate the Reaction of Thiiranes with Anhydrides

Another embodiment of the present invention is illustrated by the following equation:

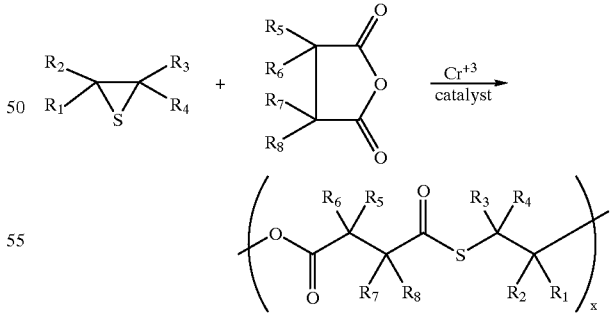

where R through $R_8$ can be made up of any combination of hydrogen, alkyl, alkene, alkyne, aryl, alkylaryl, cyano, azido, carboxy, oxo, hydroxy, halo or like kind substituted groups and x is at least 1. The result of the reaction will be the ring opening of thiirane-rings with anhydrides.

In an alternative embodiment, one or more of the reactants of the reaction are polyfunctional.

The following specific example illustrates one embodiment of the present invention:

EXAMPLE 19

Reaction of Cyclohexene Sulfide with Methyl Hexahydrophthalic Anhydride (MHHPA)

Cyclohexene sulfide, 85%, 3.3 g (24.5 mmol) and MHHPA, 4.1 g (24.4 mmol) were weighed into a 50 ml Erlenmeyer flask and thoroughly mixed. A small sample, 1.2 g was transferred into a 25 ml Erlenmeyer flask for a control. To the larger portion, 6.2 g, was added 0.8 g (1.0% Cr based on the weight of the reactants) of the $Cr^{+3}$ catalyst. The contents of both flasks were simultaneously heated to 98 to 102° C. in a hot oil bath for a period of 3 hours and 15 minutes. Samples were periodically taken from each flask for FTIR analysis. At the end of the reaction period the formation of two new carbonyl peaks (1729 $cm^{-1}$ and 1705 $cm^{-1}$) were seen to build up in the reaction flask containing the chromium catalyst but not in the control sample.

This example shows that $Cr^{+3}$ will catalyze the reaction of a thiirane (also known as epithiosulfides or ethylene sulfides) with an anhydride.

F. Further Evidence of the Unexpectedness of the Invention Results

The embodiments of the $Cr^{+3}$ invention catalyst detailed above represent unexpected results. The unexpectedness catalysis by the inventive catalyst is exemplified even further by the following specific examples which illustrate that $Cr^{+3}$ carboxylate is not able to catalyze certain reactions:

1. The Reaction of Thiiranes with Carboxylic Acids is not Accelerated with $Cr^{+3}$ Carboxylate Catalysts

EXAMPLE 20

Reaction of Cyclohexene Sulfide with 2-ethylhexanoic Acid

Cyclohexene sulfide, 85%, 3.4 g (25.3 mmol) and 2-ethylhexanoic acid, 3.5 g (24.3 mmol) were weighed into a 50 ml Erlenmeyer flask and thoroughly mixed. A small sample, 1.2 g was transferred into a 25 ml Erlenmeyer flask for a control. To the larger portion, 5.7 g, was added 0.5 g (0.7% Cr based on the weight of the reactants) of the $Cr^{+3}$ catalyst. The contents of both flasks were simultaneously heated to 98 to 102° C. in a hot oil bath for a period of 3 hours and 25 minutes. Samples were periodically taken from each flask for FTIR analysis. At the end of the reaction period, no change in composition could be seen in either reaction flask.

2. The Reaction of Tetrahydrofurans with Carboxylic Acids is not Accelerated with the $Cr^{+3}$ Carboxylate Catalysts

EXAMPLE 21

Attempted Reaction of 2-methyltetrahydrofuran with a Dimer Acid 4.7 g (7.8 mmol) of a dimer acid (as identified in Example 1, above), 1.5 g (1.9 mmol) of 2-methyl-tetrahydrofuran, and 0.4 g (0.5% Cr based on the weight of the reactants) of the $Cr^{+3}$ catalyst were weighed into a 50 ml Erlenmeyer flask and thoroughly mixed. The flask was heated to 60° C. in a hot oil bath for a period of 1⅓ hours. Samples were periodically taken for FRIR analysis. At the end of the reaction period, no new carbonyl or hydroxyl absorption was observed showing that the ring opening reaction of the 2-methyl-tetrahydrofuran did not occur.

INDUSTRIAL APPLICABILITY

It is clear that the $Cr^{+3}$ carboxylate catalysts of the invention will have wide applicability in industry to catalyze classes of reactions that heretofore have resisted effective catalytic processing. Further, the new classes of compounds produced by use of the $Cr^{+3}$ carboxylate catalyst of the invention have properties of very evident interest. In addition, the new routes of synthesis that are made available by means of the catalyst open alternate processing schemes for the chemical industry.

It should be understood that various modifications within the scope of this invention can be made by one of ordinary skill in the art without departing from the spirit thereof. We therefore wish our invention to be defined by the scope of the appended claims as broadly as the prior art will permit, and in view of the specification if need be.

We claim:

1. In a process for reacting a first component selected from the group consisting of:

(a) an aziridine, (b) an oxetane, and (c) an oxirane, with a second component selected from the group consisting of:

(i) a carboxylic acid, (ii) an anhydride, (iii) an imide, (iv) a lactone, and (v) a carbonate ester, provided that where said first component is an oxirane, said second component is not a carboxylic acid, anhydride, or imide, the improvement comprising carrying out said reaction in the presence of a catalytically effective amount of a $Cr^{+3}$ carboxylate catalyst selected from the group consisting of $C_3$–$C_{60}$, substituted and unsubstituted, straight and branch-chained, alkyl, aryl, and aralkyl carboxylate $Cr^{+3}$ salts.

2. In a process for reacting a member selected from the group consisting of a thiirane and a hydroxy compound with an anhydride, the improvement comprising carrying out said reaction in the presence of a catalytically effective amount of a $Cr^{+3}$ carboxylate catalyst selected from the group consisting of $C_3$–$C_{60}$, substituted and unsubstituted, straight and branch-chained, alkyl, aryl, and aralkyl carboxylate $Cr^{+3}$ salt.

3. The process as in claim 2, wherein said hydroxy compound is a dihydroxy ester resin.

4. The process as in claims 1 or 2, wherein said $Cr^{+3}$ carboxylate catalyst is a member selected from the group consisting of an octoate, an acetate, a butyrate, and a benzoate.

5. The process as in claims 1 or 2, wherein said $Cr^{+3}$ carboxylate catalyst is a $Cr^{+3}$ octoate.

6. The process as in claims 1 or 2, wherein the $Cr^{+3}$ content of said $Cr^{+3}$ carboxylate catalyst is from about 4% to about 8%.

7. The process as in claims 1 or 2, wherein the concentration of $Cr^{+3}$ in the reaction medium is from about 0.08% to about 2.0%, by weight, based on the combined weight of the reactants.

8. The process as in claims 1 or 2, wherein the concentration of $Cr^{+3}$ in the reaction medium is from about 0.1% to about 0.7%, by weight, based on the combined weight of the reactants.

9. The process as in claims 1 or 2, wherein said anhydride is a copolymer of maleic anhydride and styrene.

* * * * *